United States Patent
Bur et al.

(10) Patent No.: US 9,346,793 B2
(45) Date of Patent: *May 24, 2016

(54) HYDROXYLATED AMINOTRIAZOLE DERIVATIVES AS ALX RECEPTOR AGONISTS

(75) Inventors: Daniel Bur, Allschwil (CH); Olivier Corminboeuf, Allschwil (CH); Sylvaine Cren, Allschwil (CH); Corinna Grisostomi, Allschwil (CH); Xavier Leroy, Allschwil (CH); Sylvia Richard-Bildstein, Allschwil (CH)

(73) Assignee: Actelion Pharmaceuticals, LTD., Allschwil (CH)

(*) Notice: Subject to any disclaimer, the term of this patent is extended or adjusted under 35 U.S.C. 154(b) by 351 days.

This patent is subject to a terminal disclaimer.

(21) Appl. No.: 13/992,156

(22) PCT Filed: Dec. 6, 2011

(86) PCT No.: PCT/IB2011/055492
§ 371 (c)(1),
(2), (4) Date: Jun. 6, 2013

(87) PCT Pub. No.: WO2012/077051
PCT Pub. Date: Jun. 14, 2012

(65) Prior Publication Data
US 2013/0267569 A1 Oct. 10, 2013

(30) Foreign Application Priority Data

Dec. 7, 2010 (WO) ................ PCT/IB2010/055614

(51) Int. Cl.
*C07D 413/14* (2006.01)
*C07D 417/14* (2006.01)

(52) U.S. Cl.
CPC ........... *C07D 413/14* (2013.01); *C07D 417/14* (2013.01)

(58) Field of Classification Search
CPC ........................ C07D 413/14; C07D 417/14
See application file for complete search history.

(56) References Cited

U.S. PATENT DOCUMENTS

| | | | |
|---|---|---|---|
| 8,288,419 B2 | 10/2012 | Bur et al. | |
| 2004/0043904 A1 | 3/2004 | Yamaguchi et al. | |
| 2010/0331378 A1 | 12/2010 | Bur et al. | |
| 2012/0115841 A1 | 5/2012 | Bur et al. | |
| 2012/0115916 A1 | 5/2012 | Bur et al. | |

FOREIGN PATENT DOCUMENTS

| | | |
|---|---|---|
| JP | 62-234018 | 10/1987 |
| WO | 03/082314 | 10/2003 |
| WO | 2005/047899 | 5/2005 |
| WO | 2007/055941 | 5/2007 |
| WO | 2009/025793 | 2/2009 |
| WO | 2009/077954 | 6/2009 |
| WO | 2009/077990 | 6/2009 |
| WO | 2010/134014 | 11/2010 |
| WO | 2010/143116 | 12/2010 |
| WO | 2010/143158 | 12/2010 |
| WO | 2012/066488 | 5/2012 |
| WO | 2013/171687 | 11/2013 |
| WO | 2013/171694 | 11/2013 |

OTHER PUBLICATIONS

Yazawa Hiroshi et al., "β Amyloid Peptide ($AB_{42}$) is Internalized via the G-Protein-Coupled Receptor FPRL1 and Forms Fibrillar Aggregates in Macrophages",. FASEB J., (2001), 15, pp. 2454-2462.
Burli, R. W. et al., "Potent hFPRL2 (ALXR) Agonists as Potential Anti-Inflammatory Agents" Bioorganic & Medicinal Chemistry Letters (2006), 16, p. 3713-3718.
Chiang N. et al., "The Lipoxin Receptor ALX: Potent Ligand-Specific and Stereoselective Actions in Vivo" Pharmacol. Rev. (2006), 58, No. 3, pp. 463-487.
Eagles T. E et al., "Some Nitro-1,2,3-Triazoles" Organic Preparations and Procedures (1970), 2(2), pp. 117-119.
Gould, Philip, "Salt selection for basic drugs," International Journal of Pharmaceuticals, (1986) 33, pp. 201-217.
Hermitage, S. et al., "A Efficient, Practical Approach to the Synthesis of 2,4-Disubstituted Thiazoles and Oxazoles: Application to the Synthesis of GW475151" Organic Process Research (2001), 5, pp. 37-44.
Le, Y. et al., "Biologically Active Peptides Interacting with the G Protein-Coupled Formylpeptide Receptors" Protein & Peptide Letters. (2007), 14, pp. 846-853.
Mallamo et al., "Antiandrogenic Steroidal Sulfonyl Heterocyles. Utility of Electrostatic Complementarity in Defining Bioisosteric Sulfonyl Heterocycles"; Journal of Medicinal Chemistry, vol. 35, No. 10, 1992, pp. 1663-1670.
Obushak, N. D. et al.; "Heterocyclic syntheses on the basis of arylation products of unsaturated compounds: X,*3-Aryl-2-chloropropananls as reagents for the synthesis of 2-amino-1,3-thiazole derivatives;" Russian Journal of Organic Chemistry, Consultants Bureau, US LNKD-DOI: 10.123/B:RUJO.0000034976.75646.85, vol. 40, No. 3, pp. 383-389; XP009097222; ISSN: 1070-4280; Jan. 1, 2004.

(Continued)

*Primary Examiner* — Sarah Pihonak
*Assistant Examiner* — Jason A Deck
(74) *Attorney, Agent, or Firm* — Arent Fox LLP

(57) ABSTRACT

The invention relates to hydroxylated aminotriazole derivatives of formula (I),

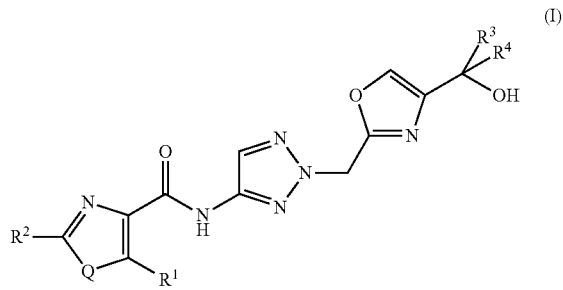

wherein Q, $R^1$, $R^2$, $R^3$ and $R^4$ are as defined in the description, their preparation and their use as pharmaceutically active compounds.

13 Claims, No Drawings

(56) References Cited

OTHER PUBLICATIONS

Newman, P., "Nitro Derivatives of Phenyl-1,2,3-triazole (1)", Heterocycles Chem (1971) 8, pp. 51-56.
Remington: The Science and Practice of Pharmacy, 21$^{st}$ Edition, Lippincott, Williams and Wilkins Publishing, The University of the Sciences in Philadelphia, 2005.
Schwab, Jan M. et al., "Lipoxins and New Lipid Mediators in the Resolution of Inflammation" Current Opinion in Pharmacology (2006), pp. 414-420.
Wermuth C. G., "Molecular Variations Based on Isosteric Replacements" The Practice of Medicinal Chemistry (1996), pp. 203-237.
Yazawa Hiroshi et al., "β Amyloid Peptide ($AB_{42}$) is Internalized via the G-Protein-Coupled Receptor FPRL1 and Forms Fibrillar Aggregates in Macrophages" Bioorg. & Med. Chem Let. (2011), 11, pp. 6608-6612.
Ying, Guoguang et al., "Humanin, a Newly identified Neuroprotective Factor, Uses the G Protein-Coupled Formylpeptide Receptor-Like-1 as a Functional Receptor", J. Immunology (2004), 172, pp. 7078-7085.
U.S. Appl. No. 12/809,545, Non Final Office Action mailed from the USPTO on Aug. 14, 2012, 24 pages.
International Search Report of PCT/IB2011/055492, mailed Feb. 2, 2012.

HYDROXYLATED AMINOTRIAZOLE DERIVATIVES AS ALX RECEPTOR AGONISTS

CROSS-REFERENCE TO RELATED APPLICATIONS

This application is the U.S. National Phase of International Application No. of PCT/IB2011/055492, filed Dec. 6, 2011, which claims priority to PCT/IB2010/055614, filed Dec. 7, 2010, the contents of each are hereby incorporated by reference in their entireties.

The present invention relates to hydroxylated aminotriazole derivatives of formula (I) and their use as pharmaceuticals. The invention also concerns related aspects including processes for the preparation of the compounds, pharmaceutical compositions containing one or more compounds of formula (I), and especially their use as ALX receptor agonists.

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogs, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). ALXR was also identified as a functional receptor of a various number of peptides, including a fragment of the prion protein, a peptide derived from gp120 of the Human Immunodeficiency Virus (HIV)-$1_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. It was also reported that humanin (HN), a peptide with neuroprotective capabilities, shares the human ALXR with Ab42 on mononuclear phagocytes and neuronal cell lines and it has been suggested that the neuroprotective activity of HN may be attributed to its competitive occupation of ALXR (Ying et al., J. Immunol., 2004, 172, 7078-7085).

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The present invention provides hydroxylated aminotriazole derivatives, which are non-peptide agonists of human ALX receptor. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Compared to aminotriazole derivatives disclosed in WO 2009/077990, which are also ALX receptor agonists, compounds of the present application demonstrated a significantly improved profile when tested for stability in human or rat plasma. In addition, it was surprisingly found, that tertiary alcohols demonstrated a high activity as ALX receptor agonists only in case they are, according to formula (I), attached to the 4-position of an oxazol-2-yl radical. Other tested heteroaryl tertiary alcohol derivatives were significantly less active. This is in contrast to acetyl derivatives disclosed in WO 2009/077990 demonstrating high activities for a variety of different heteroaryl groups.

Further aminotriazole derivatives are disclosed in WO2010/143158 and WO2010/143116; aminopyrazole derivatives as ALX receptor agonists have been described in WO 2009/077954.

Various embodiments of the invention are presented hereafter:

1) The present invention relates to hydroxylated aminotriazole derivatives of formula (I),

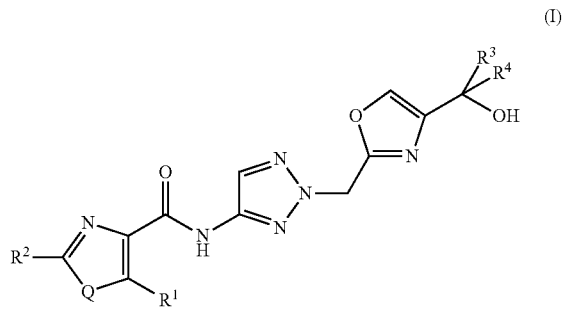

wherein
$R^1$ represents phenyl which is unsubstituted or mono-substituted with halogen, $(C_1-C_4)$alkyl, $(C_1-C_4)$alkoxy, $(C_1-C_2)$fluoroalkyl or $(C_1-C_2)$fluoroalkoxy;
$R^2$ represents hydrogen, methyl or cyclopropyl (notably hydrogen or methyl);
$R^3$ and $R^4$ both represent methyl; or $R^3$ and $R^4$ form, together with the carbon atom to which they are attached, a cyclopropyl ring; and
Q represents O, or S;
and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to four carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms. Representative examples of alkyl groups include methyl, ethyl, n-propyl, iso-propyl, n-butyl, iso-butyl, sec-butyl and tert-butyl. Preferred are $(C_1-C_3)$alkyl groups such as methyl, ethyl, n-propyl and iso-propyl. Most preferred is methyl.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred are ethoxy and methoxy. Most preferred is methoxy.

The term "fluoroalkyl" refers to an alkyl group as defined before containing one or two carbon atoms in which one or more (and possibly all) hydrogen atoms have been replaced with fluorine. The term "$(C_x-C_y)$fluoroalkyl" (x and y each being an integer) refers to a fluoroalkyl group as defined before containing x to y carbon atoms. For example a $(C_1-C_2)$fluoroalkyl group contains one or two carbon atoms in which one to five hydrogen atoms have been replaced with fluorine. Representative examples of fluoroalkyl groups include difluoromethyl, trifluoromethyl and 2,2,2-trifluoroethyl. Preferred is $(C_1)$fluoroalkyl such as trifluoromethyl and difluoromethyl. Most preferred is trifluoromethyl.

The term "fluoroalkoxy" refers to an alkoxy group as defined before containing one or two carbon atoms in which one or more (and possibly all) hydrogen atoms have been replaced with fluorine. The term "$(C_x-C_y)$fluoroalkoxy" (x and y each being an integer) refers to a fluoroalkoxy group as defined before containing x to y carbon atoms. For example a $(C_1-C_2)$fluoroalkoxy group contains one or two carbon atoms in which one to five hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy. Most preferred is trifluoromethoxy.

The term halogen means fluoro, chloro, bromo or iodo, preferably fluoro, chloro or bromo and most preferably fluoro or chloro.

2) A further embodiment of the invention relates to hydroxylated aminotriazole derivatives according to embodiment 1), wherein
$R^1$ represents phenyl which is unsubstituted or mono-substituted with halogen, $(C_1-C_4)$alkyl, $(C_1-C_4)$alkoxy, $(C_1-C_2)$fluoroalkyl or $(C_1-C_2)$fluoroalkoxy;
$R^2$ represents hydrogen or methyl;
$R^3$ and $R^4$ both represent methyl; or $R^3$ and $R^4$ form, together with the carbon atom to which they are attached, a cyclopropyl ring; and
Q represents O;
and to the salts (in particular pharmaceutically acceptable salts) of such compounds.

3) A further embodiment of the invention relates to hydroxylated aminotriazole derivatives according to any one of embodiments 1) or 2), wherein
$R^1$ represents phenyl which is unsubstituted or mono-substituted with fluoro, chloro, methyl or methoxy;
$R^2$ represents hydrogen or methyl;
$R^3$ and $R^4$ both represent methyl; and
Q represents O;
and to the salts (in particular pharmaceutically acceptable salts) of such compounds.

4) A further embodiment of the invention relates to hydroxylated aminotriazole derivatives according to any one of embodiments 1) or 2), wherein
$R^1$ represents phenyl which is unsubstituted or mono-substituted with fluoro, chloro, methyl, methoxy, trifluoromethyl or trifluoromethoxy;
and to the salts (in particular pharmaceutically acceptable salts) of such compounds.

5) A further embodiment of the invention relates to hydroxylated aminotriazole derivatives according to any one of embodiments 1) to 3), wherein
$R^1$ represents phenyl which is unsubstituted or mono-substituted with halogen, $(C_1-C_4)$alkyl or $(C_1-C_4)$alkoxy (and notably with fluoro, chloro, methyl or methoxy);
and to the salts (in particular pharmaceutically acceptable salts) of such compounds.

6) A further embodiment of the invention relates to hydroxylated aminotriazole derivatives according to any one of embodiments 1) to 3), wherein
$R^1$ represents phenyl which is unsubstituted or mono-substituted with $(C_1-C_4)$alkyl or $(C_1-C_4)$alkoxy (and notably with methyl or methoxy);
and to the salts (in particular pharmaceutically acceptable salts) of such compounds.

7) A further embodiment of the invention relates to hydroxylated aminotriazole derivatives according to any one of embodiments 1) to 6), wherein,
in case $R^1$ represents a mono-substituted phenyl group, said phenyl group is substituted in meta-position;
and to the salts (in particular pharmaceutically acceptable salts) of such compounds.

8) A further embodiment of the invention relates to hydroxylated aminotriazole derivatives according to any one of embodiments 1) to 7), wherein,
$R^2$ represents hydrogen or methyl;
and to the salts (in particular pharmaceutically acceptable salts) of such compounds.

9) A further embodiment of the invention relates to hydroxylated aminotriazole derivatives according to any one of embodiments 1) to 7), wherein,
$R^2$ represents hydrogen;
and to the salts (in particular pharmaceutically acceptable salts) of such compounds.

10) A further embodiment of the invention relates to hydroxylated aminotriazole derivatives according to any one of embodiments 1) to 7), wherein,
$R^2$ represents methyl;
and to the salts (in particular pharmaceutically acceptable salts) of such compounds.

11) A further embodiment of the invention relates to hydroxylated aminotriazole derivatives according to any one of embodiments 1) to 10), wherein,
$R^3$ and $R^4$ both represent methyl;
and to the salts (in particular pharmaceutically acceptable salts) of such compounds.

12) A further embodiment of the invention relates to hydroxylated aminotriazole derivatives according to any one of embodiments 1), 2) or 4) to 10), wherein,
$R^3$ and $R^4$ form, together with the carbon atom to which they are attached, a cyclopropyl ring;
and to the salts (in particular pharmaceutically acceptable salts) of such compounds.

13) A further embodiment of the invention relates to hydroxylated aminotriazole derivatives according to any one of embodiments 1) to 12), wherein,
Q represents O;
and to the salts (in particular pharmaceutically acceptable salts) of such compounds.

14) A further embodiment of the invention relates to hydroxylated aminotriazole derivatives according to any one of embodiments 1) or 4) to 12), wherein,
Q represents S;
and to the salts (in particular pharmaceutically acceptable salts) of such compounds.

15) Preferred compounds of formula (I) as defined in embodiment 1) are selected from the group consisting of:
2-Methyl-5-m-tolyl-oxazole-4-carboxylic acid {2-[4-(1-hydroxy-1-methyl-ethyl)-oxazol-2-ylmethyl]-2H-[1,2,3]triazol-4-yl}-amide;
2-Methyl-5-m-tolyl-oxazole-4-carboxylic acid {2-[4-(1-hydroxy-cyclopropyl)-oxazol-2-ylmethyl]-2H-[1,2,3]triazol-4-yl}-amide;
5-Phenyl-oxazole-4-carboxylic acid {2-[4-(1-hydroxy-1-methyl-ethyl)-oxazol-2-ylmethyl]-2H-[1,2,3]triazol-4-yl}-amide;
5-(4-Fluoro-phenyl)-oxazole-4-carboxylic acid {2-[4-(1-hydroxy-1-methyl-ethyl)-oxazol-2-ylmethyl]-2H-[1,2,3]triazol-4-yl}-amide;
2-Methyl-5-(3-trifluoromethyl-phenyl)-oxazole-4-carboxylic acid {2-[4-(1-hydroxy-1-methyl-ethyl)-oxazol-2-ylmethyl]-2H-[1,2,3]triazol-4-yl}-amide;
5-(3-Methoxy-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide;
5-(3-Chloro-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide;
5-(3-Chloro-phenyl)-oxazole-4-carboxylic acid {2-[4-(1-hydroxy-1-methyl-ethyl)-oxazol-2-ylmethyl]-2H-[1,2,3]triazol-4-yl}-amide;
5-(3-Methoxy-phenyl)-oxazole-4-carboxylic acid {2-[4-(1-hydroxy-1-methyl-ethyl)-oxazol-2-ylmethyl]-2H-[1,2,3]triazol-4-yl}-amide;
2-Methyl-5-phenyl-oxazole-4-carboxylic acid {2-[4-(1-hydroxy-1-methyl-ethyl)-oxazol-2-ylmethyl]-2H-[1,2,3]triazol-4-yl}-amide;
5-(3-Fluoro-phenyl)-thiazole-4-carboxylic acid {2-[4-(1-hydroxy-1-methyl-ethyl)-oxazol-2-ylmethyl]-2H-[1,2,3]triazol-4-yl}-amide;
2-Methyl-5-(3-trifluoromethoxy-phenyl)-oxazole-4-carboxylic acid {2-[4-(1-hydroxy-1-methyl-ethyl)-oxazol-2-ylmethyl]-2H-[1,2,3]triazol-4-yl}-amide;
5-(3-Fluoro-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide;
5-m-Tolyl-oxazole-4-carboxylic acid {2-[4-(1-hydroxy-1-methyl-ethyl)-oxazol-2-ylmethyl]-2H-[1,2,3]triazol-4-yl}-amide; and
2-Cyclopropyl-5-m-tolyl-oxazole-4-carboxylic acid {2-[4-(1-hydroxy-1-methyl-ethyl)-oxazol-2-ylmethyl]-2H-[1,2,3]triazol-4-yl}-amide;
or salts (in particular pharmaceutically acceptable salts) of such compounds.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 15), or pharmaceutically acceptable salts thereof, are suitable for use as medicaments. In particular, compounds of formula (I) modulate the ALX receptor, i.e. they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, cardiovascular disorders, neuroinflammation, neurological disorders, pain, prion-mediated diseases and amyloid-mediated disorders (especially Alzheimer's disease).

In particular, the compounds of formula (I) according to any one of embodiments 1) to 15), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, controlled asthma, uncontrolled asthma, mild asthma, moderate asthma, severe asthma, bronchitic asthma, exercise-induced asthma, occupational asthma and induced asthma following bacterial infection.

5) In a further embodiment the compounds of formula (I) according to any one of embodiments 1) to 15), or pharmaceutically acceptable salts thereof, are particularly suitable for the prevention or treatment of inflammatory diseases. Inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.

5c) Further inflammatory diseases also relate to diseases or conditions having an inflammatory component. Diseases or conditions having an inflammatory component include, but are not limited to, diseases and conditions affecting the eye such as uveitis (anterior, intermediate and posterior), Behçet syndrome uveitis, conjunctivitis, keratoconjunctivitis sicca, Sjögren syndrome keratoconjunctivitis sicca, and vernal conjunctivitis (and especially conjunctivitis, keratoconjunctivitis sicca, and vernal conjunctivitis); diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis (and especially systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis).

5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 15), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e g pancreatic islet cells.

Further, the compounds of formula (I) according to any one of embodiments 1) to 15), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4-v, GUN-7 wt, AG204, AG206, AG208, HCM305, HCM308, HCM342, mSTD104, and HCM309.

Further, the compounds of formula (I) according to any one of embodiments 1) to 15), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 15), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 15), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, Huntington's chorea, spinal muscular atrophy, polyglutamine diseases (such as spinobulbar muscular atrophy (Kennedy disease), spinocerebellar ataxia Type 1, 2, 3 (Machado-Joseph disease), 6, 7, 17) and cerebral malaria (and especially epilepsy, stroke, cerebral ischemia, cerebral palsy, relapsing remitting multiple sclerosis, progressive multiple sclerosis, Alpers' disease, amyotrophic lateral sclerosis (ALS), senile dementia, dementia with Lewy bodies, Rett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea).

Further, the compounds of formula (I) according to any one of embodiments 1) to 15), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 15), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to any one of embodiments 1) to 15), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, vascular dementia, HIV-related dementia, Amyotrophic Lateral Sclerosis (ALS), inclusion-body myositis (IBM), Adult Onset Diabetes, and senile cardiac amyloidosis (and especially progressive supranuclear palsy, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis).

Further, the compounds of formula (I) according to any one of embodiments 1) to 15), or pharmaceutically acceptable salts thereof, are suitable for the modulation of immune responses.

The modulation of immune responses includes, but is not limited to, methods based on the administration to a subject a composition of at least one antigen and at least one compound of formula (I) according to any one of embodiments 1) to 15), or pharmaceutically acceptable salts thereof. In some cases, the antigen-containing composition is administrated first, followed by administration of a composition of at least one compounds of formula (I) according to any one of embodiments 1) to 15), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 15), or pharmaceutically acceptable salts thereof, and the antigen, as compared to sole administration of the antigen;

2) A greater sensitivity to small amounts of antigen (e.g., toxin or pathogen) or antigens that do not habitually induce strong immune responses; and 3) More effective anti-tumor therapies.

Further, the compounds of formula (I) according to any one of embodiments 1) to 15), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, or inflammatory diseases caused by pathogenic organisms.

Especially, compounds of formula (I) according to any one of embodiments 1) to 15), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, controlled asthma, uncontrolled asthma, mild asthma, moderate asthma, severe asthma, bronchitic asthma, exercise-induced asthma, occupational asthma and induced asthma following bacterial infection (and especially acute lung injury (ALI); adult/acute respiratory distress syndrome (ARDS); and asthma of whatever type or genesis, including intrinsic (non-allergic) asthma and extrinsic (allergic) asthma, controlled asthma, uncontrolled asthma, mild asthma, moderate asthma, severe asthma, bronchitic asthma, exercise-induced asthma, occupational asthma and induced asthma following bacterial infection);

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;

3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);

4) HIV-mediated retroviral infections such as diseases and disorders caused by HIV-1 and HIV-2 strains such as GUN-4-v, GUN-7 wt, AG204, AG206, AG208, HCM305, HCM308, HCM342, mSTD104, and HCM309;

5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;

6) Neurological disorders such as stroke, cerebral ischemia, Alzheimer's disease, and Parkinson's disease;

7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);

8) Amyloid-mediated disorders;

9) Cystic fibrosis, wound healing and inflammatory diseases caused by pathogenic organisms.

The invention also relates to the use of a compound of formula (I) according to any one of embodiments 1) to 15) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 15).

A pharmaceutical composition according to the present invention contains at least one compound of formula (I) according to any one of embodiments 1) to 15) (or a pharmaceutically acceptable salt thereof) as the active agent and optionally carriers and/or diluents and/or adjuvants.

The compounds of formula (I) according to any one of embodiments 1) to 15) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 15), or a pharmaceutically acceptable salt thereof.

Any reference to a compound of formula (I) in this text is to be understood as referring also to the salts (and especially the pharmaceutically acceptable salts) of such compounds, as appropriate and expedient. The preferences indicated for the compounds of formula (I) of course apply mutatis mutandis to the salts and pharmaceutically acceptable salts of the compounds of formula (I). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$ and Q are as defined for formula (I). Other abbreviations used are defined in the experimental section.

Reactions of alcohols with methanesulfonyl chloride may result in the formation of the respective chloride or the respective mesylate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

A. Synthesis of Final Products

A.a) The compounds of formula (I) can be prepared from amines of structure 1 by reaction with the appropriate carboxylic acid chloride at a temperature about rt in a suitable solvent such as $CH_2Cl_2$ in presence of a base such as $Et_3N$ or DIPEA. The appropriate carboxylic acid chloride can be prepared at a temperature about rt from the corresponding carboxylic acid of structure 6 by reaction with a reagent such as oxalyl chloride in presence of DMF in a suitable solvent such as toluene. Alternatively, amines of structure 1 can be coupled with the appropriate carboxylic acid of structure 6 using standard amide coupling conditions such as EDC/HOBt/DMAP, or TBTU, or HBTU, or PyBOP in presence of a base such as DIPEA or Et$_3$N at a temperature about rt in a suitable solvent such as CH$_2$Cl$_2$ (or a mixture of CH$_2$Cl$_2$ and DMF) to give compounds of formula (I).

Structure 1

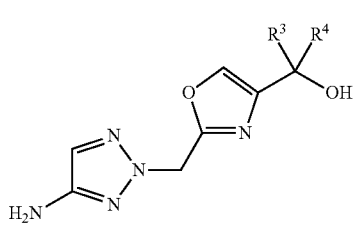

A.b) Alternatively, the compounds of formula (I) wherein R$^3$ and R$^4$ form, together with the carbon atom to which they are attached, a cyclopropyl ring may be prepared by reduction of an ester of structure 2 to the corresponding alcohol under standard reducing conditions using a reagent such as DiBAL-H in a solvent such as THF at a temperature ranging from about −78° C. to rt.

Structure 2

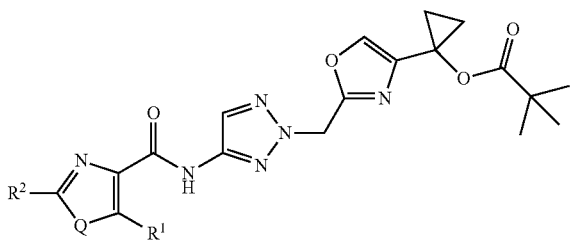

A.c) Alternatively, the compounds of formula (I) wherein R$^3$ and R$^4$ both represent methyl may be prepared by addition of a methyl Grignard reagent to a ketone of structure 3 at a temperature below rt (preferably about −78° C.) in a solvent such as THF, or, alternatively, by addition of a trialkylaluminum reagent at a temperature about 0° C. in a solvent such as CH$_2$Cl$_2$ providing the corresponding tertiary alcohol.

Structure 3

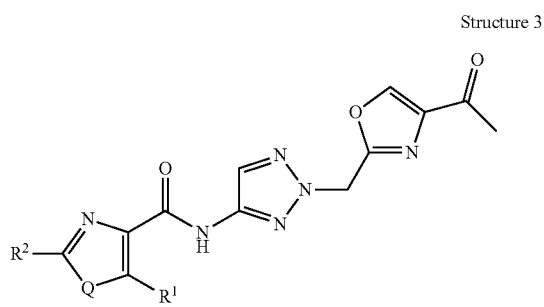

B. Synthesis of Intermediates

Compounds of structure 1 can be obtained from compounds of structure 4 by reduction of the nitro group either by hydrogenation in the presence of a metal catalyst such as Pd/C, Pt/C or PtO$_2$ at a temperature about rt in a suitable solvent such as MeOH or EtOH, or by reduction with a metal such as iron in a solvent mixture such as H$_2$O/EtOH in the presence of ammonium chloride at a temperature ranging from rt to about 95° C.

Structure 4

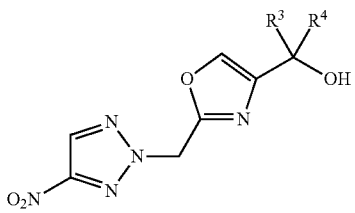

Compounds of structure 4 may be prepared by reacting compounds of structure 5 with 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) in the presence of a base such as K$_2$CO$_3$ or Cs$_2$CO$_3$ in a solvent such as acetone or AcCN at a temperature about rt or 80° C. (with or without addition of tetrabutylammonium bromide). Alternatively, the reaction may be performed in the presence of a base such as DIPEA in a solvent such as DMF, acetone or a mixture of both at a temperature about rt or 50° C.

Structure 5

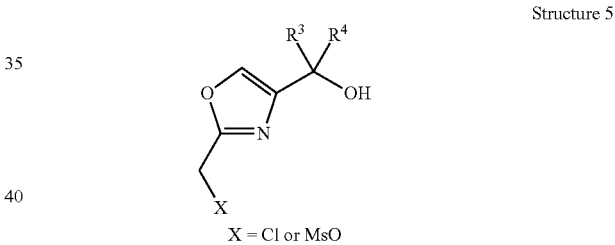

X = Cl or MsO

Compounds of structure 5 wherein R$^3$ and R$^4$ represent methyl may be prepared by addition of a methyl Grignard reagent to methyl 2-(chloromethyl)oxazole-4-carboxylate (Organic Process Research & Development 2001, 5, 37-44) at a temperature below rt (preferably about −78° C.) in a solvent such as THF, or, alternatively, addition of a trialkylaluminum reagent at a temperature about 0° C. in a solvent such as CH$_2$Cl$_2$ providing the corresponding tertiary alcohol.

Alternatively, compounds of structure 4 wherein R$^3$ and R$^4$ represent methyl may be prepared by addition of a methyl Grignard reagent on 1-(2-((4-nitro-2H-1,2,3-triazol-2-yl)methyl)oxazol-4-yl)ethanone (WO 2009/077990, page 105) at a temperature below rt (preferably about −78° C.) in a solvent such as THF, or, alternatively, addition of a trialkylaluminum reagent at a temperature about 0° C. in a solvent such as CH$_2$Cl$_2$ providing the corresponding tertiary alcohol.

Compounds of structure 2 may be prepared starting from methyl 2-(chloromethyl)oxazole-4-carboxylate (Organic Process Research & Development 2001, 5, 37-44) according to the following sequence: a) formation of the acetate by treatment with a mixture of acetic anhydride and sodium acetate in acetic acid at around 120° C. b) cleavage of the acetate using sodium methanolate c) protection of the resulting alcohol by a protecting group such as TBDMS d) cyclopropanation by treatment with tetraisopropoxytitanium (IV) and ethyl magnesium bromide e) protection of the tertiary alcohol by treatment with pivaloyl chloride in pyridine f) TBDMS deprotection using TBAF in THF g) mesylate formation by treatment with MsCl in presence of triethylamine, h) coupling with 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) in the presence of a base such as K₂CO₃ or Cs₂CO₃ in a solvent such as acetone or AcCN at a temperature about rt or 80° C. (with or without addition of tetrabutylammonium bromide). Alternatively, the reaction may be performed in the presence of a base such as DIPEA in a solvent such as DMF, acetone or a mixture of both at a temperature about rt or 50° C., i) reduction of the nitro group either by hydrogenation in the presence of a metal catalyst such as Pd/C, Pt/C or PtO₂ at a temperature about rt in a suitable solvent such as MeOH or EtOH, or by reduction with a metal such as iron in a solvent mixture such as H₂O/EtOH in the presence of ammonium chloride at a temperature ranging from rt to about 95° C., j) coupling with the appropriate carboxylic acid chloride at a temperature about rt in a suitable solvent such as CH₂Cl₂ in presence of a base such as Et₃N or DIPEA. The appropriate carboxylic acid chloride can be prepared at a temperature about rt from the corresponding carboxylic acid of structure 6 by reaction with a reagent such as oxalyl chloride in presence of DMF in a suitable solvent such as toluene. Alternatively, coupling with the appropriate carboxylic acid of structure 6 using standard amide coupling conditions such as EDC/HOBt/DMAP, or TBTU, or HBTU or PyBOP in presence of a base such as DIPEA or Et₃N at a temperature about rt in a suitable solvent such as CH₂Cl₂ (or a mixture of CH₂Cl₂ and DMF)

Compounds of structure 3 may be prepared by reacting 1-(2-((4-amino-2H-1,2,3-triazol-2-yl)methyl)oxazol-4-yl) ethanone (WO 2009/077990, page 105) with the appropriate carboxylic acid chloride at a temperature about rt in a suitable solvent such as CH₂Cl₂ in presence of a base such as Et₃N or DIPEA. The appropriate carboxylic acid chloride can be prepared at a temperature about rt from the corresponding carboxylic acid of structure 6 by reaction with a reagent such as oxalyl chloride in presence of DMF in a suitable solvent such as toluene. Alternatively, 1-(2-((4-amino-2H-1,2,3-triazol-2-yl)methyl)oxazol-4-yl)ethanone can be coupled with the appropriate carboxylic acid of structure 6 using standard amide coupling conditions such as EDC/HOBt/DMAP, or TBTU, or HBTU or PyBOP in presence of a base such as DIPEA or Et₃N at a temperature about rt in a suitable solvent such as CH₂Cl₂.

Acids of structure 6 are commercially available, well known in the art or prepared according to the methods described in WO 2009/077990 (pages 112 to 116) or in analogy.

Structure 6

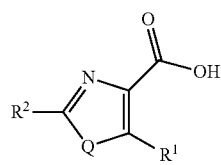

1-(2-((4-Nitro-2H-1,2,3-triazol-2-yl)methyl)oxazol-4-yl) ethanone (described in WO 2009/077990) may also be prepared by reacting methanesulfonic acid 4-acetyl-oxazol-2-ylmethyl ester (described in WO 2009/077990, page 105) with 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) in the presence of a base such as K₂CO₃ or Cs₂CO₃ in a solvent such as acetone or AcCN at a temperature about rt or 80° C. (with or without addition of tetrabutylammonium bromide). Alternatively, the reaction may be performed in the presence of a base such as DIPEA in a solvent such as DMF, acetone or a mixture of both at a temperature about rt or 50° C.

EXPERIMENTAL PART

Abbreviations (as Used Herein and in the Description Above)

Ac acetyl
AcCN acetonitrile
AlMe₃ trimethyl aluminium
aq. aqueous
COAD chronic obstructive airway disease
COLD chronic obstructive lung disease
COPD chronic obstructive pulmonary disease
DAD diode array detector
DCC N,N'-dicyclohexylcarbodiimide
DIPEA diisopropylethylamine
DiBAL-H di-iso-butylaluminum hydride
DMAP 4-N,N-dimethylaminopyridine
DMEM dulbecco's modified eagle's medium
DMF dimethylformamide
DMSO dimethylsulfoxide
EA ethyl acetate
EC₅₀ half maximal effective concentration
EDC    N-(3-dimethylaminopropyl)-W-ethyl-carbodiimide hydrochloride
ELSD evaporative light-scattering detection
eq. equivalent(s)
Et ethyl
Ether or Et₂O diethylether
Et₃N triethylamine
EtOH ethanol
FC flash column chromatography on silica gel
FLIPR fluorescence imaging plate reader
FPRL1 formyl-peptide receptor like-1
GSH glutathione
h hour(s)
HBTU    O-(benzotriazol-1-yl)-N,N,N',N'-tetramethyluronium hexafluorophosphate
(Hank's) BSS (hanks') balanced salt solution
hept heptane
HIV human immunodeficiency virus
HLM human liver microsomes
HOBt hydroxybenzotriazole
HPLC high performance liquid chromatography
IU international units
LC-MS liquid chromatography-mass spectrometry
lem emission wavelength
lex excitation wavelength
Me methyl
MeOH methanol
min minute(s)
mM millimolar
μM micromolar
MS mass spectrometry
Ms methanesulfonyl
NADPH nicotinamide adenine dinucleotide phosphate
nm nanometer
nM nanomolar NMR nuclear magnetic resonance
org. organic
p para
PG protecting group
PTFE polytetrafluoroethylene
PyBOP benzotriazol-1-yl-oxy-tris-pyrrolidino-phosphonium-hexafluorophosphate
Rochelle's salt potassium sodium tartrate
RCP radiochemical purity
rf retention factor
rpm rotation per minute
rt room temperature
sat. saturated
SDS sodium dodecyl sulfate
sol. solution
TBAF tetra-n-butylammonium fluoride
TBDMS tert-butyl-dimethyl-silyl
TBTU O-(benzotriazol-1-yl)-N,N,N',N'-tetramethyluronium tetrafluoroborate
TFA trifluoroacetic acid
THF tetrahydrofuran
TLC thin layer chromatography
$t_R$ retention time
UV ultra violet
V is visible I Chemistry General.

All temperatures are stated in degrees Celsius (° C.). Unless otherwise indicated, the reactions take place at rt.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm); elution with EA, hept, $CH_2Cl_2$, $CHCl_3$, MeOH, $NH_4OH$ or mixtures thereof.

LC-MS-conditions 10 (if not indicated otherwise): Analytical: Dionex HPG-3000 Binary Pump, MS: Thermo MSQ MS, DAD: Dionex PDA 3000, ELSD: PolymerLab ELS 2100. Column: Ascentis Express C18 2.7 µm, 2.1×30 mm ID from Sigma-Aldrich, thermostated in the Dionex TCC-3000 compartment. Eluents: A: $H_2O$+0.05% $NH_4OH$+2% AcCN; B: AcCN. Method: Gradient: 5% B→95% B over 2.00 min. Flow: 1.8 mL/min. Detection: UV/Vis and/or ELSD, and MS, $t_R$ is given in min.

LC-MS-conditions 02 (if not indicated otherwise): Analytical: Thermo Finnigan MSQ Plus MS with Agilent 1100 Binary Pump and DAD. Column: Zorbax SB-AQ 5 µm, 4.6×50 mm ID from Agilent Technologies. Eluents: A: $H_2O$+0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions 04 (if not indicated otherwise): Analytical: Dionex P680, MS: Thermo MSQ Plus, DAD: Agilent G1315A, ELSD: Sedere Sedex 85. Column: Waters XBridge C18 5 µm, 4.6×50 mm. Eluents: A: water/NH3 ([NH3]=13 mmol); B: AcCN. Method: Gradient: 5% B→95% B over 0.75 min. Flow: 4.5 mL/min. Detection: UV/Vis and/or ELSD, and MS, $t_R$ is given in min.

LC-MS-conditions 06 (if not indicated otherwise): Analytical. Pump: Dionex HPG-3200RS, MS: Thermo MSQ Plus, DAD: Dionex DAD-3000RS, ELSD: Sedere Sedex 85. Column: Atlantis T3 5 µM, 4.6×30 mm ID from Waters, thermostated (40° C.) in the Dionex TCC-3200 compartment. Eluents: A: $H_2O$+0.04% TFA; B: AcCN. Method: Gradient: 5% B→95% B over 1.00 min. Flow: 4.5 mL/min. Detection: UV/Vis and/or ELSD, and MS, $t_R$ is given in min.

HPLC preparative: X-Bridge C18 5 µm, 50×19 mm ID from Waters. Eluents: A: $H_2O$+0.5% $NH_4OH$; B: AcCN; Gradient: 10% B→90% B over 5 min. Flow: 40.0 mL/min. Detection: UV/Vis and/or ELSD, and MS, $t_R$ is given in min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

General Procedures

General Procedure 1 (GP1): Amide Coupling:

In a vial equipped with a magnetic stir bar and under an inert atmosphere ($N_2$), the desired acid (1.5 eq) was treated sequentially with a) 2-(2-((4-amino-2H-1,2,3-triazol-2-yl)methyl)oxazol-4-yl)propan-2-ol (0.1 mmol, 1.0 eq.) 0.4M in a 4 to 1 mixture of $CH_2Cl_2$/DMF (0.25 mL), b) a mixture of HOBT (2.0 eq.), DMAP (0.25 eq.) and DIPEA (2.0 eq) in $CH_2Cl_2$ (0.25 mL) and c) EDC.HCl (1.5 eq) in $CH_2Cl_2$ (0.5 mL). The reaction mixture was then stirred for 12 h at rt. The resulting solution was loaded into a syringe containing isolute HM-N (diatomaceous earth from International Sorbent Technology) (800 mg) conditioned with water (0.6 mL) and the syringe was washed with $CH_2Cl_2$ (5×1 mL). The solvent was removed under reduced pressure. Purification by preparative HPLC afforded the desired material.

Synthesis of Reference Compounds

Reference Compound 1

N-(2-((4-(2-Hydroxypropan-2-yl)thiazol-2-yl)methyl)-2H-1,2,3-triazol-4-yl)-2-methyl-5-(m-tolyl)oxazole-4-carboxamide

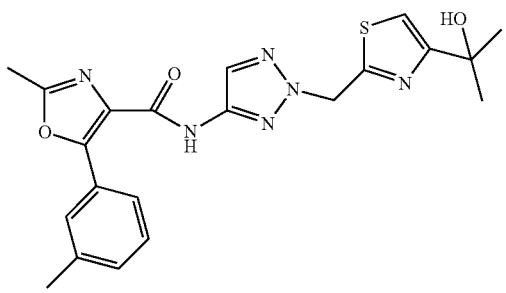 [SMILES: Cc1cccc(-c2oc(C)nc2C(=O)Nc2cnn(Cc3nc(C(C)(C)O)cs3)n2)c1]

In a flame dried round-bottomed flask equipped with a magnetic stir bar and under inert atmosphere ($N_2$), a solution of N-(2-((4-acetylthiazol-2-yl)methyl)-2H-1,2,3-triazol-4-yl)-2-methyl-5-(m-tolyl)oxazole-4-carboxamide (example 75 from WO 2009/077990; 50 mg, 0.12 mmol) in $CH_2Cl_2$ (1.1 mL) was treated at 0° C. with $AlMe_3$ (0.3 mL of a 1.0M solution in heptane, 0.3 mmol) and the resulting mixture was stirred for 2 h at 0° C. The reaction mixture was carefully poured into a sat. aq. solution of ammonium chloride (5 mL) and diluted with CH$_2$Cl$_2$ (10 mL). 1N HCl (5 mL) was then added. The layers were separated and the org. phase was dried over Na$_2$SO$_4$, filtered and the solvents were removed under reduced pressure. Purification of the residue by FC (1:1 hept-EA) gave the title compound as a colorless oil: TLC: rf (1:1 hept-EA)=0.20. LC-MS-conditions 02: t$_R$=0.88 min, [M+H]$^+$=438.94.

Synthesis of Intermediates

N-(2-((4-Acetyloxazol-2-yl)methyl)-2H-1,2,3-triazol-4-yl)-2-methyl-5-(m-tolyl)oxazole-4-carboxamide

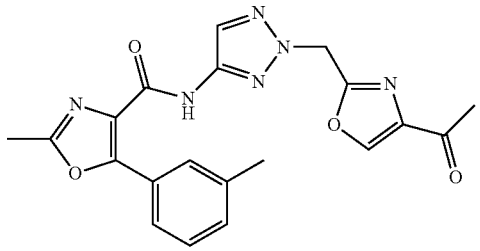 [SMILES: CC(=O)c1coc(Cn2ncc(NC(=O)c3nc(C)oc3-c3cccc(C)c3)n2)n1]

In a flame dried round-bottomed flask equipped with a magnetic stir bar and under inert atmosphere (N$_2$), a solution of 2-methyl-5-(m-tolyl)oxazole-4-carboxylic acid (WO 2009/077990) (1.38 g, 6.33 mmol) in dry toluene (63 mL) was treated with DMF (0.02 mL, 0.3 mmol) followed by oxalyl chloride (0.84 mL, 9.50 mmol) and the reaction mixture was stirred at rt for 50 min. The solvent was then removed under reduced pressure. The resulting acid chloride was dissolved in CH$_2$Cl$_2$ (23 mL) and added dropwise to a solution of 1-(2-((4-amino-2H-1,2,3-triazol-2-yl)methyl)oxazol-4-yl)ethanone (WO 2009/077990) (1.31 g, 6.33 mmol) and DIPEA (3.3 mL, 18.99 mmol) in CH$_2$Cl$_2$ (40 mL) and the resulting mixture was stirred at rt overnight. Water was added, the layers were separated, and the aq. layer was extracted three times with CH$_2$Cl$_2$. The combined org. layers were washed with brine, dried over MgSO$_4$, filtered, and the solvent was removed under reduced pressure. Purification of the residue by FC (4:6 hept-EA) gave the title compound which was re-crystallized from hot EtOH to give a white solid: TLC: rf (4:6 hept-EA)=0.35. LC-MS-conditions 02: t$_R$=0.99 min, [M+H]$^+$=407.22.

Methyl 2-(acetoxymethyl)oxazole-4-carboxylate

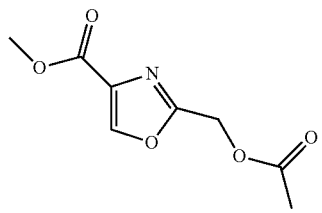

In a flame dried round-bottomed flask equipped with a magnetic stir bar and under inert atmosphere (N$_2$), a solution of methyl 2-(chloromethyl)oxazole-4-carboxylate (Organic Process Research & Development 2001, 5, 37-44) (20.00 g, 113.91 mmol) in acetic acid (80 mL) was treated with acetic anhydride (8.0 mL) followed by sodium acetate (39.72 g, 484.14 mmol). The reaction mixture was stirred at 120° C. for 3 h. EA (400 mL) was added at rt and the suspension was neutralized with sat. aq. sodium carbonate. The layers were separated and the aq. layer was extracted with EA (2×400 mL). The combined org. layers were dried over Na$_2$SO$_4$, filtered, and the solvents were removed under reduced pressure to give the title compound as a white solid. LC-MS-conditions 06: t$_R$=0.48 min, [M+H]$^+$=200.41.

Methyl 2-(hydroxymethyl)oxazole-4-carboxylate

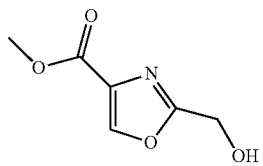

In a flame dried round-bottomed flask equipped with a magnetic stir bar and under inert atmosphere (N$_2$), sodium (1.32 g, 57.42 mmol) was added portionwise to MeOH (145 mL). Methyl 2-(acetoxymethyl)oxazole-4-carboxylate (23.30 g, 116.99 mmol) was then added and the reaction mixture was stirred for 1 h at rt. Sat. aq. NH$_4$Cl (760 mL) was then added and the mixture was extracted with EA (2×760 mL). The combined org. layers were dried over MgSO$_4$, filtered, and the solvents were removed under reduced pressure to give the title compound as a white solid: TLC: rf (9:1 hept-EA)=0.33. LC-MS-conditions 06: t$_R$=0.31 min, [M+H]$^+$=158.15.

Methyl 2-(((tert-butyldimethylsilyl)oxy)methyl)oxazole-4-carboxylate

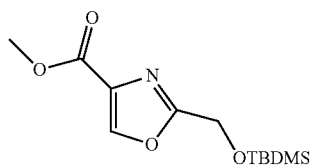 [SMILES: COC(=O)c1coc(CO[Si](C)(C)C(C)(C)C)n1]

In a flame dried round-bottomed flask equipped with a magnetic stir bar and under inert atmosphere (N$_2$), a solution of methyl 2-(hydroxymethyl)oxazole-4-carboxylate (12.00 g, 76.37 mmol) in THF (360 mL) was treated with imidazole (10.40 g, 152.75 mmol) followed by tert-butyldimethylsilyl chloride (23.02 g, 152.75 mmol) and the resulting mixture was stirred at rt for 2.5 h. EA (360 mL) and sat. aq. NH$_4$Cl (360 mL) were added. The layers were separated and the aq. layer was extracted with EA (360 mL). The combined org. layers were dried over MgSO$_4$, filtered, and the solvents were removed under reduced pressure. Purification of the residue by FC (7:3 hept-EA) gave the title compound as a white solid: TLC: rf (7:3 hept-EA)=0.44. LC-MS-conditions 06: $t_R$=0.98 min, [M+H]$^+$=272.38.

1-(2-(((tert-Butyldimethylsilyl)oxy)methyl)oxazol-4-yl)cyclopropanol

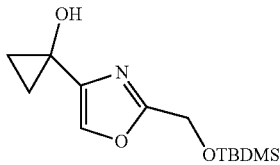 [SMILES: CC(C)(C)[Si](C)(C)OCc1nc(C2(O)CC2)co1]

In a flame dried round-bottomed flask equipped with a magnetic stir bar and under inert atmosphere (N$_2$), a solution of method 2-(((tert-butyldimethylsilyl)oxy)methyl)oxazole-4-carboxylate (3.00 g, 11.05 mmol) in THF (110 mL) was treated with tetraisopropoxytitanium (IV) (3.27 mL, 11.05 mmol). To the resulting solution at rt, was added, over 30 min, via syringe pump, ethyl magnesium bromide (18.4 mL of a 3M sol. in ether, 55.27 mmol) and the resulting solution was stirred at rt for 3 h. EA (100 mL) and 1N HCl (50 mL) were added. The layers were separated and the aq. layer was extracted with EA (2×100 mL) and the combined org. layers were washed with sat. aq. sodium bicarbonate (200 mL), brine (200 mL). The org. layer was dried over Na$_2$SO$_4$, filtered, and the solvents were removed under reduced pressure. Purification of the residue by FC (4:1 hept-EA) gave the title compound as a yellow oil: TLC: rf (4:1 hept-EA)=0.28. LC-MS-conditions 06: $t_R$=0.92 min, [M+H]$^+$=270.41.

1-(2-(((tert-Butyldimethylsilyl)oxy)methyl)oxazol-4-yl)cyclopropyl pivalate

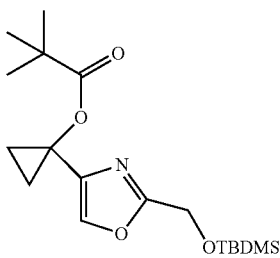 [SMILES: CC(C)(C)C(=O)OC1(c2coc(CO[Si](C)(C)C(C)(C)C)n2)CC1]

In a flame dried round-bottomed flask equipped with a magnetic stir bar and under inert atmosphere (N$_2$), a solution of 1-(2-(((tert-butyldimethylsilyl)oxy)methyl)oxazol-4-yl)cyclopropanol (509 mg, 1.89 mmol) in pyridine (2.0 mL) was treated with pivaloyl chloride (0.28 mL, 2.27 mmol) and the reaction mixture was stirred at rt overnight. Sat. aq. NH$_4$Cl (10 mL) was added followed by EA (10 mL). The org. layer was washed with a CuSO$_4$ sol. (2×15 mL) followed by brine (10 mL). The layers were separated and the org. layer was dried over MgSO$_4$, filtered, and the solvents were removed under reduced pressure. Purification of the residue by FC (9:1 hept-EA) gave the title compound as a colorless oil: TLC: rf (9:1 hept-EA)=0.35. LC-MS-conditions 06: $t_R$=1.19 min, [M+H]$^+$=354.18.

1-(2-(Hydroxymethyl)oxazol-4-yl)cyclopropyl pivalate

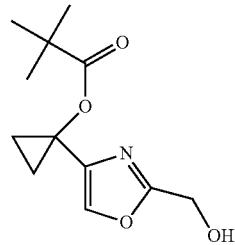 [SMILES: CC(C)(C)C(=O)OC1(c2coc(CO)n2)CC1]

In a flame dried round-bottomed flask equipped with a magnetic stir bar and under inert atmosphere (N$_2$), a solution of 1-(2-(((tert-butyldimethylsilyl)oxy)methyl)oxazol-4-yl)cyclopropyl pivalate (450 mg, 1.27 mmol) in THF (13.0 mL) at 0° C. was treated with TBAF (2.55 ml of a 1M solution in THF, 2.55 mmol) and the reaction mixture was stirred at 0° C. for 30 min. The reaction mixture was diluted with EA (30 mL), the layers were separated and the org. layer was washed sequentially with sat. aq. NH$_4$Cl and brine. The org. layer was dried over MgSO$_4$, filtered, and the solvents were removed under reduced pressure. Purification of the residue by FC (1:1 hept-EA) gave the title compound as a colorless oil: TLC: rf (1:1 hept-EA)=0.29. LC-MS-conditions 06: $t_R$=0.69 min, [M+H]$^+$=240.11.

1-(2-(((Methylsulfonyl)oxy)methyl)oxazol-4-yl)cyclopropyl pivalate

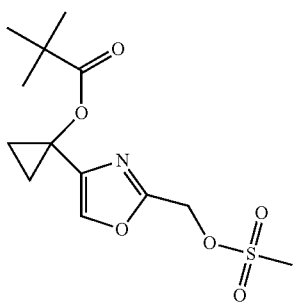 [SMILES: CC(C)(C)C(=O)OC1(c2coc(COS(C)(=O)=O)n2)CC1]

In a flame dried round-bottomed flask equipped with a magnetic stir bar and under inert atmosphere (N$_2$), a solution of 1-(2-(hydroxymethyl)oxazol-4-yl)cyclopropyl pivalate (288 mg, 1.20 mmol) at 0° C. in CH$_2$Cl$_2$ (12.0 mL) was treated Et$_3$N (0.22 mL, 1.57 mmol) followed by DMAP (15 mg, 0.12 mmol). Methanesulfonyl chloride (0.11 mL, 1.44 mmol) was then added dropwise and the reaction mixture was stirred for 1 h at rt. Water (5 mL) was added, the layers were separated, and the org. phase was dried over Na$_2$SO$_4$, filtered, and the solvent was removed under reduced pressure to give the title compound as a yellow oil. LC-MS-conditions 06: $t_R$=0.84 min, [M+H]$^+$=318.19.

1-(2-((4-Nitro-2H-1,2,3-triazol-2-yl)methyl)oxazol-4-yl)cyclopropyl pivalate

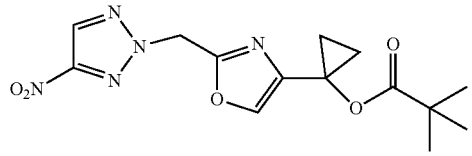 [SMILES: CC(C)(C)C(=O)OC1(c2coc(Cn3ncc([N+](=O)[O-])n3)n2)CC1]

In a flame dried round-bottomed flask equipped with a magnetic stir bar and under inert atmosphere (N$_2$), a solution of 1-(2-(((methylsulfonyl)oxy)methyl)oxazol-4-yl)cyclopropyl pivalate (400 mg, 1.26 mmol) in DMF (3.0 mL) was added to a solution of 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) (1.80 g of a 8% solution in DMF, 1.26 mmol) in DMF (3.0 mL) pre-treated for 30 min with DIPEA (0.43 mL, 2.53 mmol) and the reaction mixture was stirred overnight at 50° C. Water (20 mL), followed by EA (20 mL) were added. The layers were separated and the org. layer was washed with water (3×10 mL), dried over Na$_2$SO$_4$, filtered, and the solvents were removed under reduced pressure. Purification of the residue by FC (7:3 hept-EA) gave the title compound as a yellow oil: TLC: rf (7:3 hept-EA)=0.34. LC-MS-conditions 06: $t_R$=0.91 min, [M+H]$^+$=336.22.

1-(2-((4-Amino-2H-1,2,3-triazol-2-yl)methyl)oxazol-4-yl)cyclopropyl pivalate

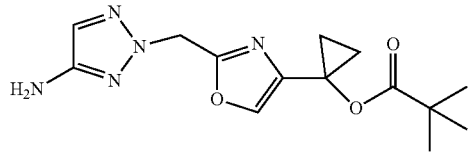

In a flame dried round-bottomed flask equipped with a magnetic stir bar and under inert atmosphere (N$_2$), a mixture of 1-(2-((4-nitro-2H-1,2,3-triazol-2-yl)methyl)oxazol-4-yl)cyclopropyl pivalate (150 mg, 0.45 mmol), iron powder (76 mg, 1.34 mmol) and NH$_4$Cl (121 mg, 2.24 mmol) in a mixture of EtOH (2.0 mL) and water (1.0 mL) was stirred at 85° C. for 15 min. The reaction mixture was filtered while hot and concentrated under reduced pressure. CH$_2$Cl$_2$ (5.0 mL) was added followed by 1N NaOH (5.0 mL). The layers were separated and the aq. layer was extracted with CH$_2$Cl$_2$ (2×5 mL). The combined org. extracts were dried over MgSO$_4$, filtered, and the solvents were removed under reduced pressure to give the title compound as a yellow oil. LC-MS-conditions 06: $t_R$=0.73 min; [M+H]$^+$=306.04.

1-(2-((4-(2-Methyl-5-(m-tolyl)oxazole-4-carboxamido)-2H-1,2,3-triazol-2-yl)methyl)oxazol-4-yl)cyclopropyl pivalate

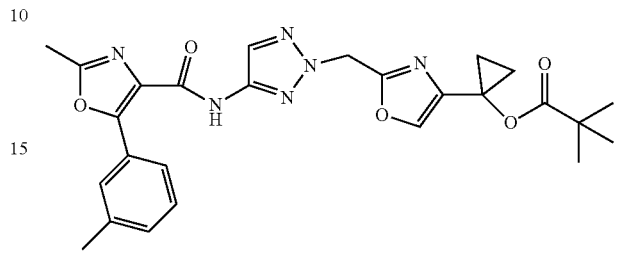

In a flame dried round-bottomed flask equipped with a magnetic stir bar and under inert atmosphere (N$_2$), a mixture of 2-methyl-5-(m-tolyl)oxazole-4-carboxylic acid (WO 2009/077990) (92 mg, 0.42 mmol) in CH$_2$Cl$_2$ (2.0 mL) was treated successively with DMAP (13 mg, 0.11 mmol), HOBt (69 mg, 0.51 mmol), EDC.HCl (203 mg, 1.06 mmol) and DIPEA (0.29 mL, 1.69 mmol) and the mixture was stirred at rt for 30 min. A solution of 1-(2-((4-amino-2H-1,2,3-triazol-2-yl)methyl)oxazol-4-yl)cyclopropyl pivalate (129 mg, 0.42 mmol) in CH$_2$Cl$_2$ (2.0 mL) was then added and the reaction mixture was stirred at rt overnight. The reaction mixture was then diluted with CH$_2$Cl$_2$ (10 mL), the layers were separated and the org. layer was washed with water (10 mL), dried over MgSO$_4$, filtered and the solvent was removed under reduced pressure. Purification of the residue by FC (2:1 hept-EA) gave the title compound as a white foam: TLC: rf (2:1 hept-EA)=0.25. LC-MS-conditions 06: $t_R$=1.10 min, [M+H]$^+$=505.37.

2-(2-(Chloromethyl)oxazol-4-yl)propan-2-ol

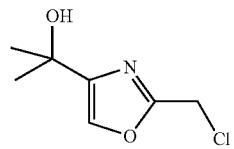

In a flame dried round-bottomed flask equipped with a magnetic stir bar and under inert atmosphere (N$_2$), a solution of methyl 2-(chloromethyl)oxazole-4-carboxylate (Organic Process Research & Development 2001, 5, 37-44) (13.00 g, 74.04 mmol) in THF (433 mL) was treated dropwise at 0° C. with methylmagnesium chloride (51.8 mL of a 3.0 M solution in THF, 155.49 mmol) and the resulting orange solution was stirred for 1.5 h at 0° C. The reaction mixture was carefully poured over an ice-chilled sat. aq. NH$_4$Cl solution (300 mL). It was extracted with EA (3×200 mL) and the combined org. layers were washed with brine (300 mL) dried over MgSO$_4$, filtered and the solvent was removed under reduced pressure.

Purification of the residue by FC (6:4 hept-EA) gave the title compound as a yellow oil: TLC: rf (6:4 hept-EA)=0.24. LC-MS-conditions 06: $t_R$=0.49.

2-(2-((4-Nitro-2H-1,2,3-triazol-2-yl)methyl)oxazol-4-yl)propan-2-ol

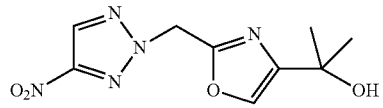

In a flame dried round-bottomed flask equipped with a magnetic stir bar and under inert atmosphere ($N_2$), a solution of 2-(2-(chloromethyl)oxazol-4-yl)propan-2-ol (1.32 g, 7.51 mmol) in DMF (22.0 mL) was added to a solution of 4-nitro-2H-[1,2,3]triazole (T. E. Eagles et al. *Organic preparations and procedures* 2 (2), 117-119, 1970; P. N. Neuman *J. Heterocycl. Chem.* 8, 51-56, 1971) (12.84 g of a 8% solution in DMF, 9.01 mmol) in DMF (22.0 mL) pre-treated for 30 min with DIPEA (2.57 mL, 15.01 mmol) and the reaction mixture was stirred overnight at 50° C. Water (60 mL), followed by EA (60 mL) were added. The layers were separated and the org. layer was washed with water (3×60 mL), dried over $MgSO_4$, filtered, and the solvents were removed under reduced pressure. Purification of the residue by FC (4:6 hept-EA) gave the title compound as an orange oil: TLC: rf (4:6 hept-EA)=0.30. LC-MS-conditions 06: $t_R$=0.55 min.

2-(2-((4-Amino-2H-1,2,3-triazol-2-yl)methyl)oxazol-4-yl)propan-2-ol

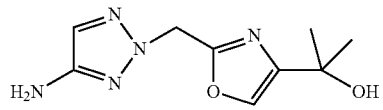 [SMILES: CC(C)(O)c1coc(Cn2ncc([N+](=O)[O-])n2)n1]

In a flame dried round-bottomed flask equipped with a magnetic stir bar and under inert atmosphere ($N_2$), a mixture of 2-(2-((4-nitro-2H-1,2,3-triazol-2-yl)methyl)oxazol-4-yl)propan-2-ol (2.40 g, 10.75 mmol), iron powder (1.82 g, 32.25 mmol) and $NH_4Cl$ (2.90 g, 53.76 mmol) in a mixture of EtOH (70 mL) and water (35 mL) was stirred at 85° C. for 15 min. The reaction mixture was filtered while hot and concentrated under reduced pressure. $CH_2Cl_2$ (110 mL) was added followed by 1N NaOH (65 mL). The layers were separated and the aq. layer was extracted with $CH_2Cl_2$ (5×50 mL). The combined org. extracts were dried over $MgSO_4$, filtered, and the solvents were removed under reduced pressure to give the title compound as an orange oil. LC-MS-conditions 06: $t_R$=0.35 min; $[M+H]^+$=224.00.

PREPARATION OF EXAMPLES

Example 1

2-Methyl-5-m-tolyl-oxazole-4-carboxylic acid {2-[4-(1-hydroxy-1-methyl-ethyl)-oxazol-2-ylmethyl]-2H-[1,2,3]triazol-4-yl}-amide In a flame dried round-bottomed flask equipped with a magnetic stir bar and under inert atmosphere ($N_2$), a solution of N-(2-((4-acetyloxazol-2-yl)methyl)-2H-1,2,3-triazol-4-yl)-2-methyl-5-(m-tolyl)oxazole-4-carboxamide (622 mg, 1.53 mmol) in $CH_2Cl_2$ (15 mL) was treated at 0° C. with $AlMe_3$ (2.3 mL of a 2.0M solution in heptane, 4.6 mmol) and the resulting mixture was stirred for 2 h at 0° C. The reaction mixture was carefully poured into a sat. aq. solution of ammonium chloride (10 mL) and diluted with $CH_2Cl_2$ (20 mL). 1N HCl (10 mL) was then added. The layers were separated and the org. phase was dried over $Na_2SO_4$, filtered and the solvents were removed under reduced pressure. Purification of the residue by FC (3:7 hept-EA) gave the title compound as a white solid: TLC: rf (3:7 hept-EA)=0.28. LC-MS-conditions 06: $t_R$=0.85 min, $[M+H]^+$=423.17.

Example 2

2-Methyl-5-m-tolyl-oxazole-4-carboxylic acid {2-[4-(1-hydroxy-cyclopropyl)-oxazol-2-ylmethyl]-2H-[1,2,3]triazol-4-yl}-amide In a flame dried round-bottomed flask equipped with a magnetic stir bar and under inert atmosphere ($N_2$), a solution of 1-(2-((4-(2-methyl-5-(m-tolyl)oxazole-4-carboxamido)-2H-1,2,3-triazol-2-yl)methyl)oxazol-4-yl)cyclopropyl pivalate (70 mg, 0.14 mmol) in THF (1.4 mL) was treated at 0° C. with DiBAL-H (0.7 mL of a 1M solution in THF, 0.70 mmol) and the resulting solution was stirred for 3.5 h at 0° C. The reaction mixture was poured onto a Rochelle's salt aq. solution (14 mL) and the mixture was vigorously stirred for 2 h at rt. The two layers were separated and the aq. phase was extracted with EA (14 mL). The combined org. layers were dried over $MgSO_4$, filtered and the solvents were removed under reduced pressure. Purification of the residue by FC (4:6 hept-EA) gave the title compound as a yellow oil: TLC: rf (4:6 hept-EA)=0.30. LC-MS-conditions 06: $t_R$=0.86 min, $[M+H]^+$=421.22

Example 3

5-Phenyl-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-phenyloxazole-4-carboxylic acid (commercially available). LC-MS-conditions 10: $t_R$=0.95 min, $[M+H]^+$=395.12.

Example 4

5-(4-Fluoro-phenyl)-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-(4-fluorophenyl)oxazole-4-carboxylic acid (WO 2009/077990, page 114). LC-MS-conditions 10: $t_R$=0.99 min, $[M+H]^+$=413.08.

Example 5

2-Methyl-5-(3-trifluoromethyl-phenyl)-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 2-methyl-5-(3-(trifluoromethyl)phenyl)oxazole-4-carboxylic acid (WO 2009/077990, page 113). LC-MS-conditions 10: $t_R$=1.22 min, $[M+H]^+$=477.02.

Example 6

5-(3-Methoxy-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-(3-methoxyphenyl)-2-methyl-oxazole-4-carboxylic acid (WO 2009/077990, page 112). LC-MS-conditions 10: $t_R$=1.06 min, [M+H]$^+$=439.08.

Example 7

5-(3-Chloro-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-(3-chlorophenyl)-2-methyl-oxazole-4-carboxylic acid (WO 2009/077990, page 113). LC-MS-conditions 10: $t_R$=1.18 min, [M+H]$^+$=443.02.

Example 8

5-(3-Chloro-phenyl)-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-(3-chlorophenyl)oxazole-4-carboxylic acid (WO 2009/077990, page 114). LC-MS-conditions 10: $t_R$=1.08 min, [M+H]$^+$=429.02.

Example 9

5-(3-Methoxy-phenyl)-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-(3-methoxyphenyl)oxazole-4-carboxylic acid (WO 2009/077990, page 114). LC-MS-conditions 10: $t_R$=0.98 min, [M+H]$^+$=425.09.

Example 10

2-Methyl-5-phenyl-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 2-methyl-5-phenyloxazole-4-carboxylic acid (WO 2009/077990, page 113). LC-MS-conditions 10: $t_R$=1.04 min, [M+H]$^+$=409.13.

Example 11

5-(3-Fluoro-phenyl)-thiazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-(3-fluorophenyl) thiazole-4-carboxylic acid (WO 2009/077990, page 115). LC-MS-conditions 10: $t_R$=0.97 min, [M+H]$^+$=429.03.

Example 12

2-Methyl-5-(3-trifluoromethoxy-phenyl)-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 2-methyl-5-(3-(trifluoromethoxy)phenyl)oxazole-4-carboxylic acid (WO 2009/077990, page 113). LC-MS-conditions 10: $t_R$=1.26 min, [M+H]$^+$=493.04.

Example 13

5-(3-Fluoro-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-(3-fluorophenyl)-2-methyloxazole-4-carboxylic acid (WO 2009/077990, page 112). LC-MS-conditions 10: $t_R$=1.09 min, [M+H]$^+$=427.08.

Example 14

5-m-Tolyl-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 5-(m-tolyl)oxazole-4-carboxylic acid (WO 2009/077990, page 114). LC-MS-conditions 10: $t_R$=1.05 min, [M+H]$^+$=409.09.

Example 15

2-Cyclopropyl-5-m-tolyl-oxazole-4-carboxylic acid {2-[4-(1-hydroxy-1-methyl-ethyl)-oxazol-2-ylmethyl]-2H-[1,2,3]triazol-4-yl}-amide Synthesized according to GP1 using 2-cyclopropyl-5-(m-tolyl)oxazole-4-carboxylic acid (prepared as for 2-cyclopropyl-5-phenyl-oxazole-4-carboxylic acid in WO 2009/077990, page 114, but starting from ethyl 3-oxo-3-(m-tolyl)propanoate). LC-MS-conditions 10: $t_R$=1.29 min, [M+H]$^+$=449.1.

II. Biological Assays

In Vitro Assay

The ALX receptor agonistic activity of the compounds of formula (I) is determined in accordance with the following experimental method.

Experimental Method:

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1,000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 μM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50,000 cells in 70 μl per well and sedimented by centrifugation at 1,000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturers standard instructions, adding 4 µl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities with respect to the ALX receptor ($EC_{50}$ values) of exemplified compounds are displayed in Table 1.

TABLE 1

| Compound | $EC_{50}$ [nM] |
| --- | --- |
| Example 1:<br>2-Methyl-5-m-tolyl-oxazole-4-carboxylic acid {2-[4-(1-hydroxy-1-methyl-ethyl)-oxazol-2-ylmethyl]-2H-[1,2,3]triazol-4-yl}-amide | 11.8 |
| Example 2:<br>2-Methyl-5-m-tolyl-oxazole-4-carboxylic acid {2-[4-(1-hydroxy-cyclopropyl)-oxazol-2-ylmethyl]-2H-[1,2,3]triazol-4-yl}-amide | 7.6 |
| Example 3:<br>5-Phenyl-oxazole-4-carboxylic acid {2-[4-(1-hydroxy-1-methyl-ethyl)-oxazol-2-ylmethyl]-2H-[1,2,3]triazol-4-yl}-amide | 8.0 |
| Example 4:<br>5-(4-Fluoro-phenyl)-oxazole-4-carboxylic acid {2-[4-(1-hydroxy-1-methyl-ethyl)-oxazol-2-ylmethyl]-2H-[1,2,3]triazol-4-yl}-amide | 51.0 |
| Example 5:<br>2-Methyl-5-(3-trifluoromethyl-phenyl)-oxazole-4-carboxylic acid {2-[4-(1-hydroxy-1-methyl-ethyl)-oxazol-2-ylmethyl]-2H-[1,2,3]triazol-4-yl}-amide | 21.7 |
| Example 6:<br>5-(3-Methoxy-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide | 12.7 |

TABLE 1-continued

| Compound | $EC_{50}$ [nM] |
| --- | --- |
| Example 7:<br>5-(3-Chloro-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide | 10.1 |
| Example 8:<br>5-(3-Chloro-phenyl)-oxazole-4-carboxylic acid {2-[4-(1-hydroxy-1-methyl-ethyl)-oxazol-2-ylmethyl]-2H-[1,2,3]triazol-4-yl}-amide | 17.8 |
| Example 9:<br>5-(3-Methoxy-phenyl)-oxazole-4-carboxylic acid {2-[4-(1-hydroxy-1-methyl-ethyl)-oxazol-2-ylmethyl]-2H-[1,2,3]triazol-4-yl}-amide | 17.2 |
| Example 10:<br>2-Methyl-5-phenyl-oxazole-4-carboxylic acid {2-[4-(1-hydroxy-1-methyl-ethyl)-oxazol-2-ylmethyl]-2H-[1,2,3]triazol-4-yl}-amide | 10.3 |
| Example 11:<br>5-(3-Fluoro-phenyl)-thiazole-4-carboxylic acid {2-[4-(1-hydroxy-1-methyl-ethyl)-oxazol-2-ylmethyl]-2H-[1,2,3]triazol-4-yl}-amide | 82.3 |
| Example 12:<br>2-Methyl-5-(3-trifluoromethoxy-phenyl)-oxazole-4-carboxylic acid {2-[4-(1-hydroxy-1-methyl-ethyl)-oxazol-2-ylmethyl]-2H-[1,2,3]triazol-4-yl}-amide | 32.3 |
| Example 13:<br>5-(3-Fluoro-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide | 13.2 |
| Example 14:<br>5-m-Tolyl-oxazole-4-carboxylic acid {2-[4-(1-hydroxy-1-methyl-ethyl)-oxazol-2-ylmethyl]-2H-[1,2,3]triazol-4-yl}-amide | 11.3 |
| Example 15:<br>2-Cyclopropyl-5-m-tolyl-oxazole-4-carboxylic acid {2-[4-(1-hydroxy-1-methyl-ethyl)-oxazol-2-ylmethyl]-2H-[1,2,3]triazol-4-yl}-amide | 52.9 |

Comparative Test Results

It was surprisingly found, that tertiary alcohols demonstrated a high activity as ALX receptor agonists only in case they are, according to formula (I), attached to the 4-position of an oxazol-2-yl radical. Other tested heteroaryl tertiary alcohol derivatives were significantly less active. This is in contrast to acetyl derivatives disclosed in WO 2009/077990 demonstrating high activities for a variety of different heteroaryl groups (table 2, $EC_{50}$ values from intracellular calcium measurements).

TABLE 2

(agonistic activities as measured in the above described assay)

| compound falling within formula (I) of WO09/077990 | $EC_{50}$ [nM] | hydroxylated compounds | $EC_{50}$ [nM] |
| --- | --- | --- | --- |
| 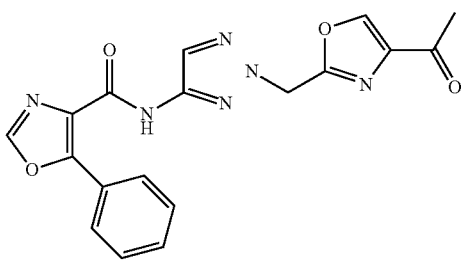<br>(example 91) | 0.7 | 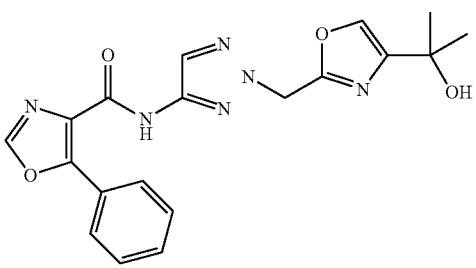<br>(example 3) | 8.0 |

TABLE 2-continued (agonistic activities as measured in the above described assay)

| compound falling within formula (I) of WO09/077990 | EC$_{50}$ [nM] | hydroxylated compounds | EC$_{50}$ [nM] |
|---|---|---|---|
| (example 75) | 2.2 | (reference compound 1) | 245 |

Assay for Covalent Binding Between Reactive Metabolites and Proteins Using Human Liver Microsomes The objective of the described covalent binding assay is to determine the amount of covalent binding between reactive metabolites and proteins of human liver microsomes (HLM) per hour following incubation in the presence of an NADPH regenerating system. The measured covalent binding rate is expressed in pmol bound drug equivalent/mg protein/h. It is a well-known advantage if compounds have a low tendency to bind covalently to proteins.

Incubation

The radiolabelled compounds ($^3$H or $^{14}$C) were incubated at a concentration of 10 μM in a single 96 well plate with 1.0 mg/mL of human liver microsomes in 0.1 M phosphate buffer (pH 7.4). To this end, a volume of 2.5 μL 1 mM stock solution prepared in the respective solvent (ethanol) was added to a final volume of 250 μL. Incubations were performed in the absence or presence of the NADPH-regenerating system with glucose-6-phosphate dehydrogenase (20 IU/ml dehydrogenase, 25 μl with 11 mM NADP sodium salt, 100 mM glucose-6-phosphate disodium salt, 100 mM MgCl$_2$ in 0.1 M Tris buffer, pH 7.4) and additionally in the absence or presence of 5 mM GSH to trap reactive intermediates. An initial blank value without NADPH without incubation was also determined to determine unspecific rapid binding. Reactions were initiated by addition of 25 μL of an NADPH-regenerating system and terminated after one hour by adding 200 μL of the incubation mixture on a multiscreen deep well solvinert 96 hydrophobic PTFE filter plate (Millipore, Zug, Switzerland) containing 260 μL of ice-cold acetonitrile. The precipitation of microsomal proteins was completed by shaking the plate at 600 rpm at a temperature of 15° C. for 15 min. Finally, the precipitated incubation was stored at 4° C. for 15 min in the fridge.

Proteins and filtrates were separated by centrifugation at 1800 g for 20 min at 10° C. The protein pellet was washed to remove unspecific binding with 800 μL of methanol/0.1% sulfuric acid (v/v) by centrifugation at 1500 g, 10° C. and 2 min. The washing step was repeated six times. The washed protein pellet was redissolved by addition of 500 μL of aqueous 0.1% (w/v) NaOH/1% (w/v) SDS. The filter plate was shaken at 400 rpm for 45 min at 60° C. and centrifugated at 2000 g for 20 min at 35° C. This step was repeated once and the protein solutions were combined.

For the determination of total radioactivity, an aliquot of 400 μL protein solution was mixed with 4 mL of liquid scintillation cocktail (Irga Safe plus, Perkin Elmer, Zürich, Switzerland) and analyzed using a Tricarb 2300 TR liquid scintillation analyzer (Perkin Elmer) with luminescence correction and on-line quenching correction by means of an external standard ($^{133}$Ba). For the determination of total protein content, an aliquot of 20 μL protein solution was analyzed using the BCA protein assay kit (Perbio Science Switzerland SA, Lausanne, Switzerland). The amount of covalent binding to microsomal proteins was calculated as follows: Dividing the determined amount of bound drug equivalent with NADPH (background subtracted by the amount of bound drug equivalent without NADPH) by the calculated amount of protein of redissolved washed protein pellet in each well gives the amount of bound drug equivalent in pmol/mg protein per hour.

Plasma Stability Assay

Rat or human plasma adjusted at pH 7.4 with lactic acid or ammonium hydroxide, were equilibrated at 37° C. under orbital shaking in an incubator containing 5% CO$_2$. The reaction was initiated by the addition of 1 μM of compounds (1 μl of 1 mM stock solution in DMSO in 999 μl of plasma). At the beginning and after 30 min, 1 h, 2 h, 4 h, 6 h and 24 h, aliquots (30 μl) were transferred in a 96 well plate containing 90 μl MeOH placed on ice to stop the reaction. After vortexing for 20 min at 1400 rpm on an Eppendorf thermomixer the plates were centrifuged at 3220 g for 20 min at 4° C. and the supernatants were analyzed with LC-MSMS. Calibration samples in plasma containing 0.1% of dichlorvos were prepared and analysed in parallel to the incubation samples to allow the quantification. Half lives in hours were then calculated.

The following results have been obtained using the plasma stability assay as described above:

| compound falling within formula (I) of WO09/077990 | species | Plasma stability: $t_{1/2}$ [h] | compound of formula (I) | species | Plasma stability: $t_{1/2}$ [h] |
|---|---|---|---|---|---|
| (example 91) | human rat | 8.4 2.8 | (example 3) | human rat | >24 >24 |
| (example 2) | human rat | 3.6 4.1 | (example 2) | human rat | >24 >24 |
| (example 1) | human rat | 3.6 4.1 | (example 1) | human rat | >24 >24 |

The invention claimed is:

1. A compound of the formula (I),

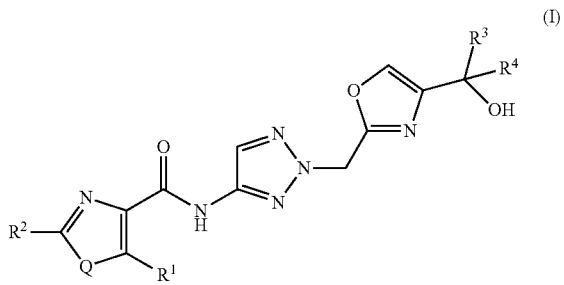

wherein

R[1] represents phenyl which is unsubstituted or mono-substituted with halogen, (C₁-C₄)alkyl, (C₁-C₄)alkoxy, (C₁-C₂)fluoroalkyl or (C₁-C₂)fluoroalkoxy;

R[2] represents hydrogen, methyl or cyclopropyl;

R[3] and R[4] both represent methyl; or R[3] and R[4] form, together with the carbon atom to which they are attached, a cyclopropyl ring; and Q represents O, or S;

or a salt thereof.

2. The compound according to claim 1, wherein

R[1] represents phenyl which is unsubstituted or mono-substituted with halogen, (C₁-C₄)alkyl, (C₁-C₄)alkoxy, (C₁-C₂)fluoroalkyl or (C₁-C₂)fluoroalkoxy;

R[2] represents hydrogen or methyl;

R[3] and R[4] both represent methyl; or R[3] and R[4] form, together with the carbon atom to which they are attached, a cyclopropyl ring; and Q represents O;

or a salt thereof.

3. The compound according to claim 1, wherein

R[1] represents phenyl which is unsubstituted or mono-substituted with halogen, (C₁-C₄)alkyl or (C₁-C₄)alkoxy;

or a salt thereof.

4. The compound according to claim 1, wherein when R[1] represents a mono-substituted phenyl group, said phenyl group is substituted in meta-position;

or a salt thereof.

5. The compound according to claim 1, wherein R[2] represents hydrogen or methyl;

or a salt thereof.

6. The compound according to claim 1, wherein R[3] and R[4] both represent methyl;

or a salt thereof.

7. The compound according to claim 1, wherein R[3] and R[4] form, together with the carbon atom to which they are attached, a cyclopropyl ring;

or a salt thereof.

8. The compound according to claim 1, wherein Q represents O;

or a salt thereof.

9. The compound according to claim 1, wherein the compound is:

2-Methyl-5-m-tolyl-oxazole-4-carboxylic acid {2-[4-(1-hydroxy-1-methyl-ethyl)-oxazol-2-ylmethyl]-2H-[1,2,3]triazol-4-yl}-amide;

2-Methyl-5-m-tolyl-oxazole-4-carboxylic acid {2-[4-(1-hydroxy-cyclopropyl)-oxazol-2-ylmethyl]-2H-[1,2,3]triazol-4-yl}-amide;

5-Phenyl-oxazole-4-carboxylic acid {2-[4-(1-hydroxy-1-methyl-ethyl)-oxazol-2-ylmethyl]-2H-[1,2,3]triazol-4-yl}-amide;

5-(4-Fluoro-phenyl)-oxazole-4-carboxylic acid {2-[4-(1-hydroxy-1-methyl-ethyl)-oxazol-2-ylmethyl]-2H-[1,2,3]triazol-4-yl}-amide;

2-Methyl-5-(3-trifluoromethyl-phenyl)-oxazole-4-carboxylic acid {2-[4-(1-hydroxy-1-methyl-ethyl)-oxazol-2-ylmethyl]-2H-[1,2,3]triazol-4-yl}-amide;

5-(3-Methoxy-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide;

5-(3-Chloro-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide;

5-(3-Chloro-phenyl)-oxazole-4-carboxylic acid {2-[4-(1-hydroxy-1-methyl-ethyl)-oxazol-2-ylmethyl]-2H-[1,2,3]triazol-4-yl}-amide;

5-(3-Methoxy-phenyl)-oxazole-4-carboxylic acid {2-[4-(1-hydroxy-1-methyl-ethyl)-oxazol-2-ylmethyl]-2H-[1,2,3]triazol-4-yl}-amide;

2-Methyl-5-phenyl-oxazole-4-carboxylic acid {2-[4-(1-hydroxy-1-methyl-ethyl)-oxazol-2-ylmethyl]-2H-[1,2,3]triazol-4-yl}-amide;

5-(3-Fluoro-phenyl)-thiazole-4-carboxylic acid {2-[4-(1-hydroxy-1-methyl-ethyl)-oxazol-2-ylmethyl]-2H-[1,2,3]triazol-4-yl}-amide;

2-Methyl-5-(3-trifluoromethoxy-phenyl)-oxazole-4-carboxylic acid {2-[4-(1-hydroxy-1-methyl-ethyl)-oxazol-2-ylmethyl]-2H-[1,2,3]triazol-4-yl}-amide;

5-(3-Fluoro-phenyl)-2-methyl-oxazole-4-carboxylic acid {2-[4-(1-hydroxy-1-methyl-ethyl)-oxazol-2-ylmethyl]-2H-[1,2,3]triazol-4-yl}-amide;

5-m-Tolyl-oxazole-4-carboxylic acid {2-[4-(1-hydroxy-1-methyl-ethyl)-oxazol-2-ylmethyl]-2H-[1,2,3]triazol-4-yl}-amide; or 2-Cyclopropyl-5-m-tolyl-oxazole-4-carboxylic acid {2-[4-(1-hydroxy-1-methyl-ethyl)-oxazol-2-ylmethyl]-2H-[1,2,3]triazol-4-yl}-amide;

or a salt thereof.

10. A medicament comprising the compound according to claim 1, or a pharmaceutically acceptable salt thereof, and a pharmaceutically acceptable excipient.

11. A pharmaceutical composition comprising, as an active principle, a compound according to claim 1, or a pharmaceutically acceptable salt thereof, and at least one therapeutically inert excipient.

12. A method of treating a disease or condition comprising administering to a subject in need thereof a therapeutically effective amount of a compound according to claim 1, wherein the disease or condition is responsive to an ALX receptor agonist; and wherein the disease is an inflammatory disease, obstructive airway disease, allergic condition, HIV-mediated retroviral infection, cardiovascular disorder, neuroinflammation, neurological disorder, pain, prion-mediated disease or amyloid-mediated disorder or wherein the condition is the modulation of immune responses.

13. A method of treating a disease or condition comprising administering to a subject in need thereof a therapeutically effective amount of a compound according to claim 9, wherein the disease or condition is responsive to an ALX receptor agonist; and wherein the disease is an inflammatory disease, obstructive airway disease, allergic condition, HIV-mediated retroviral infection, cardiovascular disorder, neuroinflammation, neurological disorder, pain, prion-mediated disease or amyloid-mediated disorder or wherein the condition is the modulation of immune responses.

* * * * *